US006228390B1

(12) United States Patent
Kundel

(10) Patent No.: US 6,228,390 B1
(45) Date of Patent: *May 8, 2001

(54) HYDROGEL LAMINATE, BANDAGES AND COMPOSITES AND METHODS FOR FORMING THE SAME

(75) Inventor: Nikhil K. Kundel, Piscataway, NJ (US)

(73) Assignee: Johnson & Johnson Consumer Companies, Inc., Skillman, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 09/330,228

(22) Filed: Jun. 10, 1999

Related U.S. Application Data

(63) Continuation of application No. 09/137,916, filed on Aug. 20, 1998, now abandoned, which is a continuation of application No. 08/940,358, filed on Sep. 30, 1997, now abandoned, which is a continuation of application No. 08/463,147, filed on Jun. 5, 1995, now abandoned, which is a division of application No. 08/285,617, filed on Aug. 3, 1994, now Pat. No. 5,480,717, which is a continuation of application No. 07/990,722, filed on Sep. 15, 1992, now abandoned.

(51) Int. Cl.[7] ............................. A61F 13/00; B32B 5/16; C08K 3/28
(52) U.S. Cl. .................... 424/448; 424/445; 428/338; 428/483; 522/75; 522/83
(58) Field of Search ................................ 424/489, 464, 424/488, 490, 445; 428/338

(56) References Cited

U.S. PATENT DOCUMENTS 5,480,717 * 1/1996 Kundel ................................ 428/338

* cited by examiner

Primary Examiner—Thurman K. Page
Assistant Examiner—Isis Ghali

(57) ABSTRACT

The present invention provides processes by which a polymeric hydrogel can be securely adhered to a substrate to form a hydrogel laminate with greatly improved delamination resistance. The laminate is formed by casting onto a polymeric adhesive-coated substrate an aqueous solution of hydrophilic polymer, then exposing this composite to ionizing radiation which cross-links the hydrophilic polymer to form a hydrogel and also induces copolymerization of the hydrophilic polymer and the adhesive polymer.

4 Claims, 2 Drawing Sheets

HYDROGEL LAMINATE, BANDAGES AND COMPOSITES AND METHODS FOR FORMING THE SAME

This is a continuation of Ser. No. 09/137,916, filed Aug. 20, 1998, abandoned, which is a continuation of Ser. No. 08/940,358, filed Sep. 30, 1997, abandoned, which is a continuation of Ser. No. 08/463,147, filed Jun. 5, 1995, abandoned, which is a division of Ser. No. 08/285,617, filed Aug. 3, 1994, now U.S. Pat. No. 5,480,717, which is a continuation of Ser. No. 07/990,722, fled Dec. 15, 1992, abandoned.

FIELD OF THE INVENTION

This invention relates to novel processes for adhering polymeric hydrogels to an adhesive coated surface of a substrate and to novel hydrogel laminates and bandages and methods for forming the same.

BACKGROUND OF THE INVENTION

The integumentary system is the exterior organ that, although often taken for granted, is vital to physical well being. The most obvious function of the integument is to protect against infection. Any alteration in the integrity of the skin compromises this natural defense. To minimize the risk of soft tissue infection, it is desirable to protect burns and wounds from infectious agents such as airborne fungi, bacteria and viruses. Traditional gauze type dressings are inadequate because they do not exclude infectious agents. Further, exudation from many types of skin lesions is normal during the healing process. If wound exudate has dried and consolidated the gauze dressing and wound, removal of the dressing is not only painful, it interferes with the healing process.

The use of hydrogels in the treatment and management of burns and wounds is well known in the art. Hydrogel dressings are desirable, in part, because they provide protection against infectious agents. Hydrogel dressings are further desirable because wound exudate does not generally dry and consolidate with hydrogels or hydrogel laminates. Consequently, removal of a hydrogel dressing is usually neither painful nor detrimental to the healing process. It has been suggested that hydrogel dressings may be particularly desirable for treatment of burns because they may accelerate healing. Although the mechanism by which hydrogels stimulate healing is not fully elucidated, it is documented that the high water content of hydrogels enables them to effect an immediate cooling of the wound surface and to sustain the reduced temperature for up to six hours. Davis, et al., "A New Hydrogel Dressing Accelerates Second-Degree Burn Wound Healing," Poster Presentation, Wound Healing Society First Annual Meeting, Galveston, Tex., Feb. 6, 1991. In addition, water swollen hydrogels may provide a cushioning effect that helps protect the burn or wound from physical trauma.

U.S. Pat. No. 4,438,258 relates to hydrogels which may be used as interfaces between damaged skin tissue and its external environment. As disclosed therein, hydrogels may be polymerized about some type of support, such as a mesh of nylon, use d as an unsupported film spun in fibers and woven into a fabric, or used as a powder. Further, hydrogels may be used to provide a controlled release of a medical composition.

U.S. Pat. No. 4,552,138 discloses a wound dressing material of at least one layer of a polymeric, hydrophilic gel wherein the gel is cross-linked and acetalized with formaldehyde. As disclosed therein, a gel film may be formed by spreading a pre-crosslinked gel on an auxiliary carrier, drying and at the same time cross-linking the same by heat treatment. As used in this disclosure, uncrosslinked polyvinyl alcohol is dissolved in water, acidified, preferably by hydrochloric acid, and combined with an aqueous formaldehyde solution and left to react or pre-crosslink at 50–48° C. for several hours to obtain a gelatinous mass wherein no further free aldehyde can be detected. Such gel films may be placed on the wound as such, but they are preferably processed to a laminated product with one or more carrier materials and used in this form. The carrier layers are laminated into or onto the pre-crosslinked gel layer and may be further cross-linked to bond more firmly with the gel.

U.S. Pat. No. 4,554,317 discloses a synthetic hydrophilic membrane prepared by graft polymerization of hydrophilic monomers with a polyurethane substrate. This membrane is particularly useful as a wound covering material. In one embodiment of this invention, the graft polymerization is initiated by X-ray or gamma radiation or an initiator such as a cerium salt.

EPO Publication No. 0 107 376 A1 discloses a tacky, non-rigid transparent and absorbent dressing comprising a layer of cross-linked polyvinylpyrrolidone gel containing from about 75–85% water. The dressing may be prepared by dissolving between 15% and 25% by weight of polyvinylpyrrolidone in water and cross-linking the polyvinylpyrrolidone by means of ionizing radiation.

U.S. Pat. No. 4,567,006 discloses a moisture vapor permeable, adhesive surgical dressing comprising a continuous film of a hydrophilic polymer. Such a dressing is suitable for use on moist wounds because it allows water to evaporate rapidly from the wound area in the presence of an excess of exudate but, as the amount of exudate diminishes, so does the rate of evaporation. The resulting amount of exudate is enough to keep the wound moist without causing blistering of the dressing.

U.S. Pat. No. 4,798,201 discloses a surgical dressing consisting essentially of a film which carries an adhesive layer for securing the dressing to the body. This dressing is also suitable for use on exuding wounds.

U.S. Pat. No. 4,407,846 discloses a method of producing a hydrophilic membrane from a polyethylene base film by first irradiating the film of thickness not more than 150 $\mu$m with ionizing radiation in air or an oxygen atmosphere. Then, without additional radiation, acrylic acid and/or methacrylic acid present in the form of an aqueous solution is grafted onto the irradiated film.

U.S. Pat. No. 3,669,103 discloses a flexible support adapted to be caused to conform to a surface of a body, wherein the support confines a dry, solid, water-swellable, water-insoluble polymeric sorbent to absorb aqueous fluid elaborated by the body to which the support is applied. The polymer sorbent is a lightly cross-linked polymer.

U.S. Pat. No. 4,192,727 discloses a polyelectrolyte hydrogel and method for preparing the same. The polyelectrolyte hydrogel is formed by exposing an acrylate salt and acrylamide to a controlled intensity and dose of ionizing radiation to effect simultaneous cross-linking and polymerization thereof. The resulting hydrogel is an insoluble hydrophilic copolymer which can contain or absorb aqueous fluid.

U.S. Pat. No. 4,646,730 discloses a color stabilized sulfadiazine hydrogel dressing comprising a non-rigid layer of cross-linked polyvinylpyrrolidone gel having incorporated therein at least 0.1% by weight of silver sulfadiazine, which gel has been exposed to electron beam radiation and which gel also contains a color stabilizing amount of magnesium trisilicate.

U.S. Pat. No. 4,750,482 discloses a wound or burn dressing comprising a web-like substrate coated with a layer of crosslinked, water-insoluble, hydrophilic, elastomeric, pressure-sensitive adhesive gel of a gel-forming, water-soluble polymer derived from repeating units, predominantly of vinylpyrrolidone, polyethylene glycol wherein the cross-linked gel is formed by radiation cross-linking of a solution or dispersion of the polymer in the plasticizer and water. The gel retains the plasticizer within a cross-linked three-dimensional matrix of the polymer.

EPO Publication number 0 304 536 A2 discloses an occlusive wound dressing comprising an adhesive layer, a fabric layer bonded to the adhesive layer, a hydrophilic absorbent polymeric layer applied to the fabric layer, and at least one occlusive backing layer. The hydrophilic absorbent polymeric layer of this dressing is applied by pouring a monomer solution onto the fabric layer and thereafter curing to yield the polymeric layer.

Japanese Patent Application No. 57-7414 issued in the name of Saburo Otsuka and assigned to Nitto Electric Ind. KK, discloses a medicinal plaster formed by spraying or spreading a solution or dispersion containing a monomer, a medicine, a releasing aid for medicine, etc., on the surface of a tacky layer formed on a support, and then irradiating it with UV or ionizing radiation.

U.S. Pat. No. 4,871,490 discloses a method of manufacturing hydrogel dressing from synthetic and natural polymers by radiation cross-linking. The method involves an aqueous solution comprising 2–10% by weight polyvinylpyrrolidone, no more than 3% by weight of agar and 1–3% by weight of polyethylene glycol. The solution is poured into a mould to shape the dressing. The mould is then tightly closed and subjected to an ionizing radiation dose in the range of 25–40 KGy.

At present, there are a few commercially available hydrogel dressings, for example, Second Skin from Spenco and Vigilon from C.R. Bard. However, a significant problem with hydrogel dressings is that the high water content of the hydrogel makes a good adhesion with a substrate problematic. Failure to establish an adequate bond between the hydrogel and the substrate may lead to delamination and failure of the product. Consequently, currently available hydrogel dressings utilize a secondary dressing to keep the hydrogel in place. This is both inefficient and costly. It also makes the product hard to use on certain body areas. Accordingly, there is a need for adhesive bandages having a hydrogel pad securely adhered to a substrate and for processes by which a polymeric hydrogel can be securely adhered to a substrate.

It is an object of this invention to provide hydrogel laminates with improved delamination resistance and processes by which a polymeric hydrogel can be securely adhered to an adhesive coated surface of a substrate. It is a further object of this invention to develop improved adhesive bandages having absorbent hydrogel pads.

SUMMARY OF THE INVENTION

These objects have been met with the present invention. This invention relates to a hydrogel laminate comprising a substrate, such as a moisture impermeable film, a layer of polymeric adhesive on at least one surface of said substrate, and, adjacent to said adhesive coating, a layer of hydrogel. The hydrogel is formed by crosslinking of one or more hydrophilic polymers. The hydrophilic polymer(s) which form the hydrogel and the base polymer(s) of the adhesive are selected so that the these polymers are capable of copolymerizing with one another, for example, upon exposure to ionizing irradiation. The laminate so formed may be used as a component in a bandage for wound dressing, and, because of the excellent delamination strength of the laminate, such bandages offer advantages over hydrogel dressings previously known.

This invention also relate to a process for forming a hydrogel laminate. In this process, a substrate is coated on at least one surface with one or more polymeric adhesives. An aqueous solution of one or more hydrophilic polymers is cast onto the coated surface of the substrate, and the resulting composite is exposed to ionizing irradiation suitable to cross-link the hydrophilic polymers to form a hydrogel and to copolymerize the base polymers of the hydrogel and of the polymeric adhesive.

DETAILED DESCRIPTION OF THE INVENTION

Figure 1:
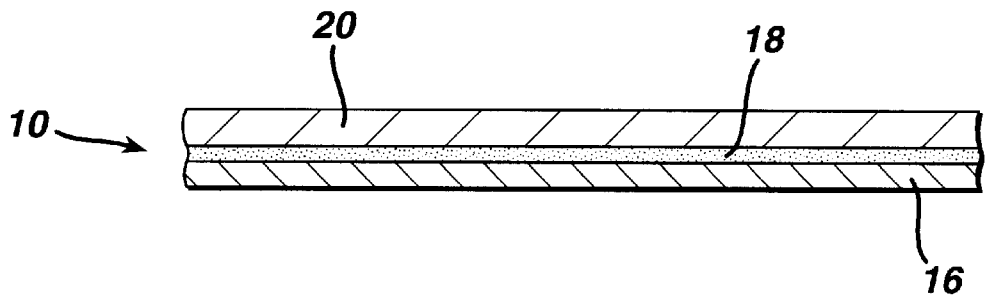
FIG. 1 is a cross sectional view of a laminate 10 comprising a substrate 16, an adhesive 18, and a hydrogel 20.

This invention relates to the preparation of hydrogel laminates, useful in absorbent products such as bandages. Hydrogels are three-dimensional networks of hydrophilic polymers, generally covalently or ionically cross-linked, which interact with aqueous solutions by swelling to some equilibrium value. These cross-linked gels are generally formed from synthetic polymers (such as polyvinylpyrrolidone, polyethyleneoxide, acrylate and methacrylate polymers and copolymers), multivalent alcohols (such as polyvinylalcohol), biopolymers (such as gelatin, agar), or combinations thereof. For the purpose of preparing bandages or wound dressings, as in this invention, additional agents may be incorporated into the hydrogel, such as, but not limited to, color stabilizers or coloring agents, and medicaments such as antibacterial agents.

A preferred hydrogel for use in this invention is crosslinked polyvinyl pyrrolidone (PVP). Best results have been achieved using PVP polymers having a viscosity average molecular weight of about 150,000–450,000 and preferably about 200,000–300,000. An especially preferred PVP polymer is PVP K-60, available from GAF Corporation, Wayne, N.J., having a viscosity average molecular weight of about 220,000. The viscosity average molecular weight was derived by the method described by W. Scholtan, *Makromol Chem.*, 7, 209 (1951) and J. Hengstenberg et al. Makromol Chem., 7, 236 (1951). The hydrogel preferably comprises about 30 to 60, preferably about 40 to 50, weight % of the polymer complemented by about 40 to 70, preferably 50 to 60, weight % water. If the molecular weight of the PVP is too high, e.g. 700,000, it is not possible to make a solution with a high enough PVP concentration, and the resulting adhesion to the polymeric adhesive layer after irradiation is not acceptable. If the molecular weight of the PVP is too low, e.g., 40,000, the PVP chains are too short to entangle with and polymerize with the polymeric adhesive layer.

The hydrogel laminate according to this invention includes a base substrate onto which the polymeric adhesive and hydrogel layer are placed. Suitable substrates include woven or nonwoven fabrics, plastic films, and laminates of woven or nonwoven fabrics and plastic films. It is generally preferred that the substrate include a moisture-impermeable thermoplastic film, examples of such films including copolyester ether elastomers, such as those sold under the tradename HYTREL by the DuPont Company, Wilmington, Del.

Polymeric adhesive is coated onto at least one surface of the substrate. As previously mentioned, the base polymer of the adhesive is selected so that it is copolymerizable with a polymer in the hydrogel, i.e., so that there are moieties on the adhesive polymer capable of covalently bonding with moieties on the hydrophilic polymer. It is also preferred that the adhesive polymer be a medical grade, pressure-sensitive adhesive which can be used to adhere the substrate to a patient's body. As an example, when the hydrogel is formed from PVP, it has been found that adhesives based on vinyl acetate, acrylic acid, acrylates or mixtures thereof are suitable since these are capable of copolymerizing with the PVP. Excellent results have been achieved using a copolymer of vinyl acetate, acrylic acid and 2-ethyl hexyl acrylate. A preferred adhesive for use with PVP hydrogel is GELVA® 2478, available from Monsanto Co., St. Louis, Mo, which is an acrylic multipolymer emulsion containing 2-propenoic acid polymer with ethenyl acetate, 2-ethylhexyl 2-propenoate and methyl 2-propenoate; water; and ethanesulfonic acid, 2-2-2 (octylphenoxy)ethoxy-ethoxy, sodium salt.

An aqueous solution of the hydrophilic polymer(s) which will crosslink to form the hydrogel is placed, or cast, onto the adhesive-coated surface of the substrate. The amount of water and polymer in the aqueous solution will be that required to produce a hydrogel of the desired water/polymer content. The composite formed by coating the polymer solution onto the adhesive-coated substrate is exposed to ionizing irradiation in a dose suitable to cross-link the hydrophilic polymer(s) to form the hydrogel and to copolymerize those hydrophilic polymer(s) and the adhesive polymer(s). Electron beam irradiation is the preferred type of ionizing irradiation. The suitable dose will, of course, depend upon the nature of the hydrophilic polymer(s) and of the adhesive polymer(s), and can be determined by one skilled in the art. Tests suggest that the electron beam irradiation dose should preferably be at least about 2.0 Mrads and no more than about 4.0 Mrads. In a preferred embodiment, the electron beam irradiation is applied in two doses. Dose rates of about 2.0 and 2.5 Mrads, 2.5 and 2.5 Mrads, 3.0 and 2.5 Mrads and 3.5 and 2.5 Mrads have been shown to directly adhere the hydrophilic polymer to the substrate, whereas adhesion was not achieved with a single dose of 4.5, 5.0, 5.5 or 6.0 Mrads. The time between each dose is not critical.

Irradiating the hydrogel laminate in two doses also provides a manufacturing benefit. After the first dose of ionizing irradiation, the hydrogen layer is partially cross-linked and has sufficient strength to be die cut into the desired shape and size. These die cut laminates may be processed into bandages using conventional techniques and then packaged in hermetically sealed containers, such as foil packs. The sealed containers are then subjected to the second dose of irradiation, which fully cross-links the hydrogel and sterilizes the product.

It is believed that the delamination resistance of the hydrogel laminates provided by this invention depends on the ability of the hydrophilic polymers of the gel and the polymers of the adhesive to copolymerize with each other to make strong covalent bonds.

Various reinforcing materials may be incorporated into the hydrogel layer for the purpose of strengthening the laminate. These materials are preferably porous or mesh-like layers about which the hydrogel polymerizes. Upon exposure to ionizing radiation, the reinforcing material is tightly bound to the hydrogel layer. The reinforcing layer is generally embedded within the hydrogel layer prior to exposure to ionizing radiation. Suitable reinforcing materials include mesh, scrims and reticulated or non-woven layers, such as nylon gauze, rayon mesh, DELNET film, available from Hercules, Inc., Wilmington, Del., and fusible fiber fabric containing polyethylene, polypropylene, polyesters and mixtures thereof.

Laminates of this invention are illustrated in FIG. 1. The hydrogel laminate 10 comprises a thin substrate 16, coated on one surface with an adhesive 18, and a hydrogel 20. The hydrogel 20 is crosslinked and covalently bonded to the adhesive 18 by electron beam irradiation.

The hydrogel laminates descried herein may be used to form bandages. The bandages may have various configurations including, for example, an island pad configuration or strip bandage configuration. In such configurations, the substrate, preferably a thermoplastic film coated on one surface with adhesive, generally extends beyond the hydrogel laminate in at least two opposing directions. Accordingly, the laminate is sized to be dimensionally smaller in length andlor width than the thermoplastic film to which it is adhered.

Figure 2:
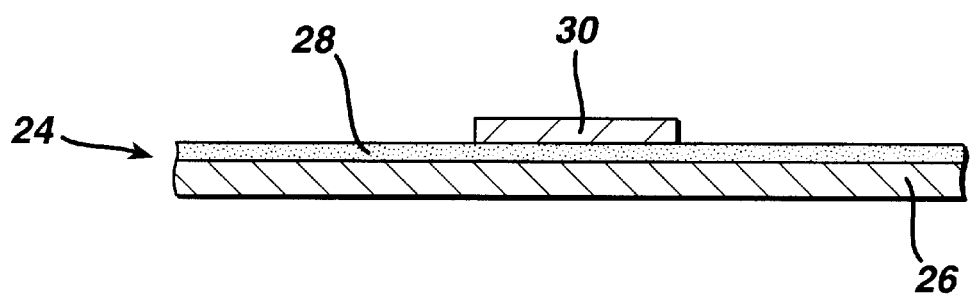
FIG. 2 is a cross sectional view of the hydrogel illustrated in FIG. 3 taken along line 1—1.
Figure 3:
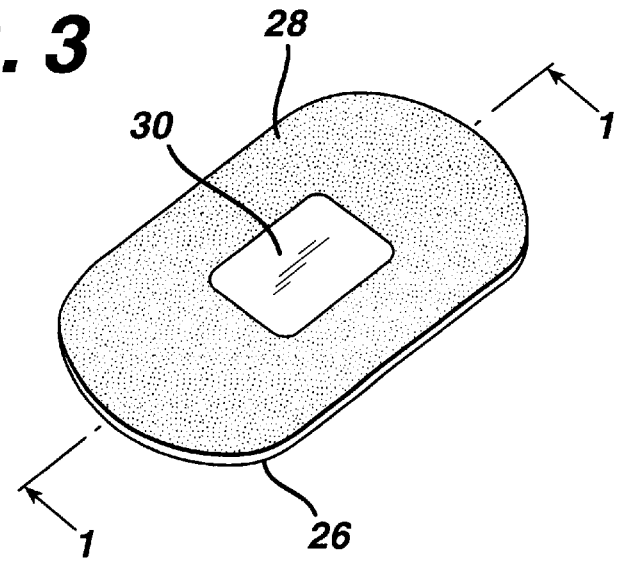
FIG. 3 is a perspective view of a bandage utilizing a hydrogel laminate of this invention.

Referring to FIGS. 2 and 3, a hydrogel bandage 24 broadly comprises a thin, polymeric film 26, coated on one surface with an adhesive 28, and a hydrogel layer or pad 30. The hydrogel 30 is crosslinked and covalently bonded to the adhesive 28 by electron beam irradiation. Adhesive 28 is preferably a medical grade, pressure-sensitive adhesive. The thin polymeric film 26 may be an embossed thermoplastic film. Suitable embossing patterns and methods for embossing thin polymeric films are known in the art and disclosed, for example, in U.S. Pat. Nos. 3,484,835, 4,298,647 and 4,376,147, incorporated herein by reference. In the illustrated bandage configuration, the hydrogel layer 30 may be in the form of an island pad, i.e., it would not be as long as either the thermoplastic film 26 or the adhesive layer 28. Portions of the adhesive layer 28 are exposed and would be used to secure the bandage 24 to the body in the same fashion as a conventional adhesive bandage. The exposed adhesive portions may be covered by release papers which may be provided with central tabs to facilitate their removal. The dressing is packaged and sterilized prior to use.

Figure 4:
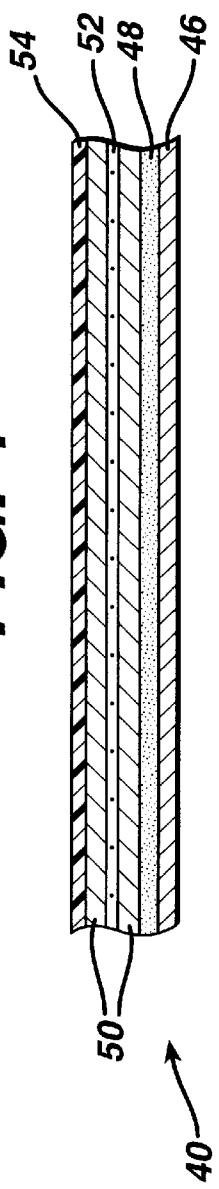
FIG. 4 is a cross sectional view of a laminate containing a reinforcing layer disposed within the hydrogel.

Laminates of this invention containing the reinforcing layer are illustrated in FIG. 4. The hydrogel laminate 40 contains a substrate 46, coated on one surface with an adhesive 48, and a hydrogel 50. Embedded with the hydrogel 50 is a reinforcing layer 52, such as a scrim. A polymeric release layer 54, such as polyethylene, is provided over the exposed surface of the hydrogel 50. The release layer 54 is peeled from the top of the laminate before use. The hydrogel laminate 40 may also be used to form bandages.

Figure 5:
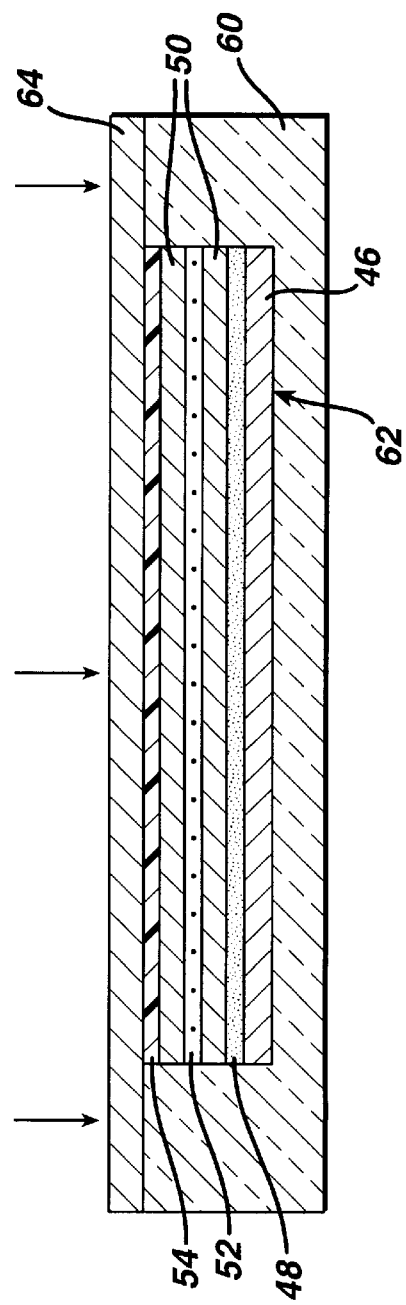
FIG. 5 is a cross sectional view of the laminate of FIG. 4 during pressing in a mold.

The mold illustrated in FIG. 5 is used to embed the reinforcing layer into the hydrogel 50. The mold consists of a bottom plate 60 having a cavity 62 and a top plate 64. The substrate 46, containing the adhesive layer 48, is placed in the bottom of the cavity. The hydrogel 50 is spread over the adhesive layer 48 and then covered with the reinforcing layer 52, such as a nylon mesh. The release layer 54 is applied over the reinforcing layer 52 before pressure is applied to the laminate by the top plate 64. As this pressure is applied, the reinforcing layer is forced into the hydrogel 50 and becomes embedded. This pressure also causes the hydrogel 50 to spread uniformly across the adhesive layer 48. The laminate is removed from the mold and then irradiated.

EXAMPLE I

A 2 mil thick copolyester ether elastomer substrate (HYTREL® 4778) was coated on one side with an acrylic multipolymer emulsion adhesive (GELVA® 2478) at 1.2 ounces per square yard ($oz/yd^2$). The adhesive coated substrate was placed in a cavity of a two piece metal mold ( 14 in.×14 in.) having the construction shown in FIG. 5. The cavity in the bottom plate was also square (10 in.×10 in.) and had a depth of 60 mil. The adhesive coated side of the substrate faced upward.

The hydrogel layer was prepared by spreading sixty grams of a 45% (by weight) solution of polyvinyl pyrrolidone having a viscosity average molecular weight of about 220,000 (PVP K-60 from GAF) over the adhesive coated side of the substrate. The PVP solution was preserved with ascorbic acid by the manufacturer.

A reinforcing layer (fusible fiber fabric containing polyethylene and polypropylene) was placed over the hydrogel. A 7 mil thick polyethylene release film was placed over the reinforcing layer.

The top plate of the mold was placed over the bottom plate for a few minutes to allow the reinforcing layer to become embedded in the hydrogel. The resulting structure was then removed from the mold.

The structure was then irradiated using a two pass election beam irradiation process. The first pass was at 2.0 Mrads while the second pass was at 2.5 Mrads.

After irradiation the adhesion between the hydrogel and the substrate was examined. Very strong adhesion was observed, and the hydrogel layer would not readily peel (by hand) from the substrate.

EXAMPLE II

Example I was repeated except that a 20% (by weight) solution of polyvinyl pyrrolidone having a viscosity average molecular weight of about 700,000 (PVP K-90 from GAF) was substituted for the PVP used in Example I.

After irradiation, the adhesion between the hydrogel and the substrate was examined. The hydrogel layer readily peeled (by hand) from the substrate.

Variations and modifications of the aforementioned bandage can, of course, be made without departing from the spirit and scope of the invention as disclosed herein, and those skilled in the art will recognize multiple utilizations of the present invention that are within the scope of this disclosure.

What is claimed is:

1. A bandage comprising a bandage substrate material, an adhesive applied to one surface of said bandage substrate material, and a hydrogel laminate secured to said adhesive applied to said one surface of said bandage substrate material, said hydrogel laminate comprising a substrate coated on at least one surface with at least one adhesive polymer and, adjacent to said adhesive polymer coating, a layer of hydrogel comprising at least one hydrophilic polymer, wherein at least one of said at least one adhesive polymer and at least one of said at least one hydrophilic polymer are copolymerized with one another.

2. The bandage of claim 1 wherein said bandage substrate material having adhesive applied thereto extends beyond said hydrogel laminate in at least two opposing directions.

3. The bandage of claim 2 wherein said adhesive applied to said one surface of said bandage substrate material is a pressure sensitive material.

4. The bandage of claim 1 wherein said bandage substrate material comprises a thermoplastic film.

\* \* \* \* \*